(12) United States Patent
Knudsen

(10) Patent No.: US 8,530,192 B2
(45) Date of Patent: Sep. 10, 2013

(54) PRODUCTION OF A POLYPEPTIDE IN A SERUM-FREE CELL CULTURE LIQUID CONTAINING PLANT PROTEIN HYDROLYSATE

(75) Inventor: Ida Molgaard Knudsen, Værløse (DK)

(73) Assignee: Novo Nordisk Healthcare AG, Zurich (CH)

( * ) Notice: Subject to any disclaimer, the term of this patent is extended or adjusted under 35 U.S.C. 154(b) by 942 days.

(21) Appl. No.: 11/815,880

(22) PCT Filed: Feb. 6, 2006

(86) PCT No.: PCT/EP2006/050669
§ 371 (c)(1),
(2), (4) Date: Jan. 9, 2008

(87) PCT Pub. No.: WO2006/084826
PCT Pub. Date: Aug. 17, 2006

(65) Prior Publication Data
US 2008/0254514 A1 Oct. 16, 2008

Related U.S. Application Data

(60) Provisional application No. 60/652,988, filed on Feb. 15, 2005.

(30) Foreign Application Priority Data

Feb. 11, 2005 (DK) ............................ 2005 00204

(51) Int. Cl.
*C12P 21/04* (2006.01)
*C12P 21/06* (2006.01)

(52) U.S. Cl.
USPC ........................................ 435/69.6; 435/69.1

(58) Field of Classification Search
USPC .............................. 435/69.6, 69.1
See application file for complete search history.

(56) References Cited

U.S. PATENT DOCUMENTS

| 6,100,061 | A | 8/2000 | Reiter et al. |
| 6,406,909 | B1 | 6/2002 | Shibuya et al. |
| 2003/0203448 | A1 | 10/2003 | Reiter et al. |

FOREIGN PATENT DOCUMENTS

| EP | 1221476 | 7/2002 |
| JP | 2004-510439 | 4/2004 |
| WO | WO 01/11021 | 2/2001 |
| WO | WO 01/23527 | 4/2001 |
| WO | WO 02/29045 | 4/2002 |
| WO | WO 02/29083 | 4/2002 |
| WO | WO 02/29084 | 4/2002 |
| WO | WO 03/029442 | 4/2003 |

OTHER PUBLICATIONS

Burteau et al., "Fortification of a Protein-Free Cell Culture Medium With Plant Peptones Improves Cultivation and Productivity of an Interferon-g-Producing Cho Cell Line", In Vitro Cell Dev. Biol.—Animal, 2003, vol. 39, pp. 291-296.
Altamirano et al., "Decoupling Cell Growth and Product Formation in Chinese Hamster Ovary Cells Through Metabolic Control", Biotechnology and Bioengineering, 2001, vol. 76, No. 4, pp. 351-360.

*Primary Examiner* — Maryam Monshipouri
(74) *Attorney, Agent, or Firm* — Rosemarie R. Wilk-Orescan

(57) ABSTRACT

The invention concerns a method for large-scale production of a polypeptide in eukaryote cells contained in a serum-free culture liquid, said method comprising (i) a propagation phase for said cells, where the cells are propagated in a first cell culture liquid, and (ii) a production phase for said cells, where the cells are present in a second cell culture medium liquid, wherein each of the cell culture liquids comprise a plant protein hydrolysate, and wherein the ratio between the concentration of the plant protein hydrolysate ($C_1$) in the first cell culture liquid and the concentration of the plant protein hydrolysate ($C_2$) in the second cell culture liquid is at least 1.5:1 ($C_1:C_2$).

20 Claims, 2 Drawing Sheets

PRODUCTION OF A POLYPEPTIDE IN A SERUM-FREE CELL CULTURE LIQUID CONTAINING PLANT PROTEIN HYDROLYSATE

CROSS-REFERENCE TO RELATED APPLICATIONS

This application is a 35 U.S.C. §371 national stage application of International Patent Application PCT/EP2006/050669 (published as WO 2006/084826 A1), filed Feb. 6, 2006, which claims priority of Danish Patent Application PA 2005 00204, filed Feb. 11, 2005. This application further claims priority under 35 U.S.C. §119 of U.S. Provisional Application 60/652,988, filed Feb. 15, 2005.

FIELD OF THE INVENTION

The present invention relates to improved methods for producing interesting polypeptides in eukaryote cells in a serum-free culture liquid.

BACKGROUND OF THE INVENTION

Methods for large-scale production of polypeptides, such as Factor VII polypeptides, in eukaryote cells are known in the art, see, e.g., WO 02/29083, WO 02/29084 and WO 03/29442.

In large-scale production of polypeptides, such as Factor VII polypeptides, it is for economical reasons desirable to prolong the production phase in order to benefit fully from the efforts put into the propagation of the cell culture. Also, it is envisaged that a more even production rate for the polypeptide over a longer period of time will render the polypeptide batch more homogeneous in that post-translational processes (e.g. glycosylation and formation of γ-carboxylic acids) are believed to proceed more accurately for a "non-stressed" cell culture.

WO 01/23527 discloses a cell culture medium for the protein-free and serum-free cultivation of cells. The medium contains a proportion of a soy hydrolysate (soy peptone).

BRIEF DESCRIPTION OF THE INVENTION

The invention relates to modification of the concentration of a plant protein hydrolysate component in the cell culture liquid during a culture, in order to, at the same time, 1) achieve optimum cell growth during the propagation phases, and 2) achieve optimum long-term stability of the culture with regard to performance in the production phase, and thereby increase the overall yield of the polypeptide in question, e.g. a Factor VII polypeptide.

A first aspect of the present invention relates to a method for large-scale production of a polypeptide in eukaryote cells contained in a serum-free culture liquid, said method comprising
(i) a propagation phase for said cells, where the cells are propagated in a first cell culture liquid, and
(ii) a production phase for said cells, where the cells are present in a second cell culture liquid,
wherein each of the cell culture liquids comprise a plant protein hydrolysate, and wherein the ratio between the concentration of the plant protein hydrolysate ($C_1$) in the first cell culture liquid and the concentration of the plant protein hydrolysate ($C_2$) in the second cell culture liquid is at least 1.5:1 ($C_1$:$C_2$).

A second aspect of the present invention relates to a method for large-scale production of a Factor VII polypeptide in eukaryote cells contained in a serum-free culture liquid, said method comprising
(i) a propagation phase for said cells, where the cells are propagated in a first cell culture liquid, and
(ii) a production phase for said cells, where the cells are present in a second cell culture liquid,
wherein each of the cell culture liquids comprise a plant protein hydrolysate, such as soy protein hydrolysate, and wherein the concentration of the plant protein hydrolysate ($C_2$) in the second cell culture liquid is in the range of 0.7-3.0 g/L.

DETAILED DESCRIPTION OF THE INVENTION

Figure 1:
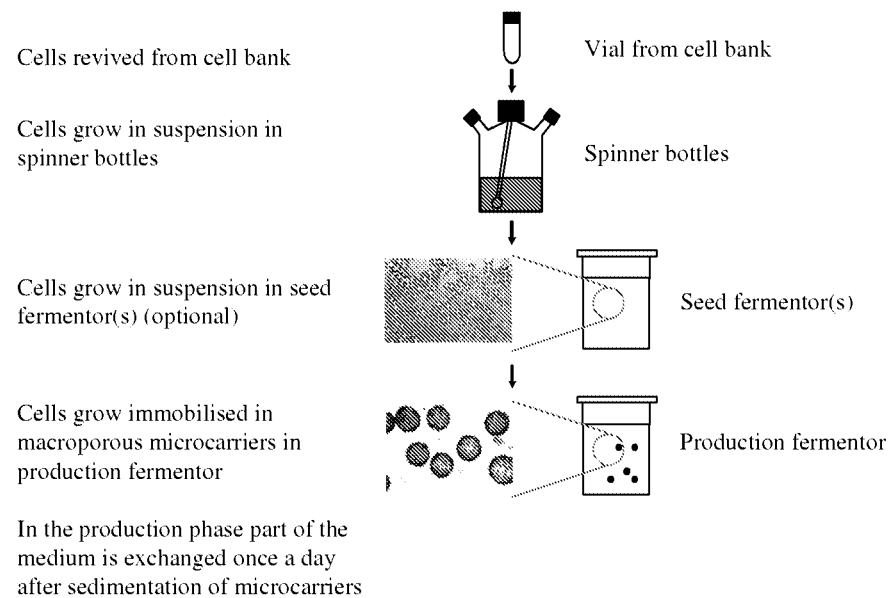
FIG. 1 illustrates a flow sheet of a cultivation process.

As mentioned above, one main aspect of the present invention relates to a method for large-scale production of a polypeptide in eukaryote cells contained in a serum-free culture liquid, said method comprising
(i) a propagation phase for said cells, where the cells are propagated in a first cell culture liquid, and
(ii) a production phase for said cells, where the cells are present in a second cell culture liquid,
wherein each of the cell culture liquids comprise a plant protein hydrolysate, and wherein the ratio between the concentration of the plant protein hydrolysate ($C_1$) in the first cell culture liquid and the concentration of the plant protein hydrolysate ($C_2$) in the second cell culture liquid is at least 1.5:1 ($C_1$:$C_2$).

By the term "large-scale production" is meant production involving a culture vessel of at least 100 L. In preferred embodiments, however, the scale is typically at least 250 L, such as at least 500 L, e.g. at least 1000 L or even 5000 L or more. The term "large-scale" may be used interchangeably with the terms "industrial-scale" and "production-scale".

The method for large-scale production of the polypeptide is typically conducted over a period of at least 120 hours, e.g. 1-26 weeks.

The present invention is to be understood as an improvement of hitherto known methods for large-scale production of a polypeptide in eukaryote cells contained in a serum-free culture liquid. It is known to use plant protein hydrolysates in such methods, but the present invention provides guidelines for improving the outcome of such methods.

A feature of the method of the main aspect of invention is to control the content of the plant protein hydrolysate in the cell culture liquids in such a manner that the propagation phase as well as the production phase is optimized. This is done by ensuring that the ratio between the concentration of the plant protein hydrolysate ($C_1$) in the first cell culture liquid (used for the propagation phase) and the concentration of the plant protein hydrolysate ($C_2$) in the second cell culture liquid (used for the production phase) is at least 1.5:1 ($C_1$:$C_2$).

Typically, the concentration of plant protein hydrolysates in the cell culture liquids is in the range 0.01-10.0 g/L. In some embodiments, a concentration ($C_1$) of around 5.0 g/L may be used during the propagation phases, and the concentration is then decreased so that the concentration of the plant protein hydrolysate ($C_2$) in the second cell culture liquid is, e.g., 1.0 g/L at initiation of the production phase. Subsequently, during the production phase the concentration might be kept at a substantially fixed level or may be alternately increased and decreased between a low and a high value, e.g. between 1.0 g/L and 2.0 g/L, in order to maintain a stable culture.

This being said, the ratio $C_1:C_2$ is preferably in the range of 2:1 to 10:1, such as 2.5:1 to 8:1 or in the range of 3:1 to 6:1.

Furthermore, the concentration $C_2$ is typically in the range of 0.2-3.5 g/L, such as in the range of 0.7-3.0 g/L, e.g. in the range of 0.9-2.5 g/L, such as in the range of 0.9-2.2 g/L, and the concentration $C_1$ is typically in the range of 4.0-10.0 g/L, such as in the range of 4.5-8.0 g/L.

As mentioned above, it is some times advantageous to slightly modify the concentration of the plant protein hydrolysate in the course of the production phase, e.g. by varying the concentration within one of the ranges given above, e.g. within the range of 0.2-3.5 g/L, such as within the range of 0.7-3.0 g/L, e.g. within the range of 0.9-2.5 g/L, such as within the range of 0.9-2.2 g/L.

Alternatively, the concentration is kept at a substantially fixed level.

The plant protein hydrolysate can be obtained from one of various sources, e.g. commercial sources. Typical types of hydrolysates are soy protein hydrolysate, wheat protein hydrolysates, pea protein hydrolysate, rice protein hydrolysate, etc. WO 01/23527 A1, which is hereby incorporated by reference, discloses the preparation and general use of a soy protein hydrolysate. Preferably, the plant protein hydrolysate is soy protein hydrolysate.

The present invention is currently not limited to the production of a particular polypeptide or to the use of a particular eukaryotic cell. However, illustrative examples of relevant polypeptides and useful eukaryotic cells are provided further below. However, in some of the currently most interesting and preferred embodiments of the invention, the polypeptide is a Factor VII polypeptide. Furthermore, in such embodiments, the eukaryotic cell is typically selected from CHO, BHK, HEK293, myeloma cells, etc.

Thus, a preferred embodiment of the main aspect of the invention relates to a method for large-scale production of a Factor VII polypeptide in eukaryote cells contained in a serum-free culture liquid, said method comprising
(i) a propagation phase for said cells, where the cells are propagated in a first cell culture liquid, and
(ii) a production phase for said cells, where the cells are present in a second cell culture liquid,
wherein the first cell culture liquid comprises a soy protein hydrolysate in a concentration of 4.0-10.0 g/L, the second cell culture liquid comprises a soy protein hydrolysate in a concentration of 0.2-3.5 g/L, and wherein the ratio between the concentration of the soy protein hydrolysate ($C_1$) in the first cell culture liquid and the concentration of the soy protein hydrolysate ($C_2$) in the second cell culture liquid is at least 1.5:1 ($C_1:C_2$).

Another aspect of the present invention relates to a method for large-scale production of a Factor VII polypeptide in eukaryote cells contained in a serum-free culture liquid, said method comprising
(i) a propagation phase for said cells, where the cells are propagated in a first cell culture liquid, and
(ii) a production phase for said cells, where the cells are present in a second cell culture liquid,
wherein each of the cell culture liquids comprise a plant protein hydrolysate, such as soy protein hydrolysate, and wherein the concentration of the plant protein hydrolysate ($C_2$) in the second cell culture liquid is in the range of 0.7-3.0 g/L. Preferably, the concentration $C_2$ is in the range of 0.9-2.5 g/L, such as in the range of 0.9-2.2 g/L.

In one embodiment, each of the cell culture liquids comprise a plant protein hydrolysate, and wherein the ratio between the concentration of the plant protein hydrolysate ($C_1$) in the first cell culture liquid and the concentration of the plant protein hydrolysate ($C_2$) in the second cell culture liquid is at least 1.5:1, e.g. in the range of 2:1 to 10:1, such as 2.5:1 to 8:1 or in the range of 3:1 to 6:1. Preferably, the concentration $C_1$ is in the range of 4.0-10.0 g/L, such as in the range of 4.5-8.0 g/L.

The results obtained so far indicate that a too high concentration of plant protein hydrolysate in the production phase will irreversibly harm the culture, thereby leading to a fairly short effective production phase (see, e.g., FIG. 2, ♦, 5.0 g/L hydrolysate), whereas a too low concentration of plant protein hydrolysate will be disadvantageous for the culture, but in a reversible manner. A too low concentration of plant protein hydrolysate in the production phase is likely to cause a reduction in the cell number and thereby the concentration of the product, but it has been shown that this can be overcome by slightly raising the concentration of plant protein hydrolysate. Without being bound to any particular theory it is believed that the profile for the concentration of the plant protein hydrolysate advantageously has the following profile:
high concentration in the propagation phase ($C_1$);
low concentration in the production phase—low level A ($C_{2A}$);
low concentration in the production phase—low level B ($C_{2B}$);
low concentration in the production phase—low level A ($C_{2A}$);
low concentration in the production phase—low level B ($C_{2B}$); etc.
where $C_1 \gg C_{2B} > C_{2A}$ and the concentrations $C_{2A}$ and $C_{2B}$ are within the concentration ranges specified for $C_2$, and wherein the first switch from low level A ($C_{2A}$) to low level B ($C_{2B}$) is conducted when a gradual decrease in the cell number has been observed over e.g. 2-5 days, and the subsequent switch from low level B ($C_{2B}$) to low level A ($C_{2A}$) is conducted when the cell number has been restored to a level approximately corresponding to the level before the decrease.

Preferably, the concentration $C_{2A}$ is in the range of 0.2-2.0 g/L, such as in the range of 0.7-1.5 g/L, e.g. in the range of 0.9-1.3 g/L, such as in the range of 0.9-1.2 g/L, and the concentration $C_{2B}$ is preferably in the range of 1.0-3.5 g/L, such as in the range of 1.1-3.0 g/L, e.g. in the range of 1.2-2.5 g/L, such as in the range of 1.2-2.2 g/L.

The term "culture liquid" is intended to mean a liquid comprising a culture of the eukaryotic cells in a suitable liquid medium. In one important embodiment, the cells are immobilized by attachment onto the surface of solid microcarriers or by attachment to or physical entrapment inside the internal structure of macroporous microcarriers. This will be explained in further details below.

Polypeptides for Large-Scale Production

As mentioned above, the present invention relates to methods relevant for the improved large-scale cultivation of eukaryote cells that express one or more proteins of interest, whether from endogenous genes or subsequent to introduction into such cells of recombinant genes encoding the protein. Such proteins include, without limitation, Factor VII polypeptides; Factor VIII; Factor IX; Factor X; Protein C; tissue factor; rennin; growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF); fibroblast growth factor such as α-FGF and β-FGF; epidermal growth factor (EGF); transforming growth factor (TGF) such as TGF-alpha and TGF-beta, insulin-like growth factor-I and -II (IGF-I and IGF-II); CD proteins such as CD-3, CD-4, CD-8, and CD-19; erythropoietin; osteoinductive factors; immunotoxins; bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressin; regulatory proteins; antibodies; and fragments of any of the above polypeptides.

In preferred embodiments of the invention, the polypeptide is a Factor VII polypeptide.

In some embodiments hereof, the cells used in practicing the invention are human cells expressing an endogenous Factor VII gene. In these cells, the endogenous gene may be intact or may have been modified in situ, or a sequence outside the Factor VII gene may have been modified in situ to alter the expression of the endogenous Factor VII gene.

In other embodiments hereof, cells from any eukaryote source are engineered to express human Factor VII from a recombinant gene.

As used herein, the terms "Factor VII polypeptide" and "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes FVII variants, Factor VII-related polypeptides, Factor VII derivatives and Factor VII conjugates exhibiting substantially the same or improved biological activity relative to wild-type human Factor VIIa.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

Such variants of Factor VII may exhibit different properties relative to human Factor VII, including stability, phospholipid binding, altered specific activity, and the like.

As used herein, "wild type human FVIIa" is a polypeptide having the amino acid sequence disclosed in U.S. Pat. No. 4,784,950.

As used herein, "Factor VII-related polypeptides" encompasses polypeptides, including variants, in which the Factor VIIa biological activity has been substantially modified, such as reduced, relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, US patents U.S. Pat. No. 6,762,286 and U.S. Pat. No. 6,693,075 (University of Minnesota); and FVII variants as disclosed in WO 01/58935, US patent U.S. Pat. No. 6,806,063, US patent application 20030096338 (Maxygen ApS), WO 03/93465 (Maxygen ApS) WO 04/029091 (Maxygen ApS), WO 04/083361

(Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, PCT/DK02/00635 (corresponding to WO 03/027147), Danish patent application PA 2002 01423 (corresponding to WO 04/029090), Danish patent application PA 2001 01627 (corresponding to WO 03/027147); WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII-K316Q/L305V/K337A-FVII, K316Q/L305V/V158D-FVII, K316Q/L305V/E296V-FVII/K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/V-FVII K L16Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/

V158T/K337A/S314E-FVII, F374Y/V158T/M298Q/ K337A/S314E-FVII, F374Y/V158T/E296V/K337A/ S314E-FVII, F374Y/L305V/V158T/E296V/M298Q-FVII, F374Y/L305V/V158T/M298Q/K337A-FVII, F374Y/ L305V/V158T/E296V/K337A-FVII, F374Y/L305V/ V158T/M298Q/S314E-FVII, F374Y/L305V/V158T/ E296V/S314E-FVII, F374Y/E296V/M298Q/K337A/ V158T/S314E-FVII, F374Y/V158D/E296V/M298Q/ K337A/S314E-FVII, F374Y/L305V/V158D/E296V/ M298Q/S314E-FVII, F374Y/L305V/E296V/M298Q/ V158T/S314E-FVII, F374Y/L305V/E296V/M298Q/ K337A/V158T-FVII, F374Y/L305V/E296V/K337A/ V158T/S314E-FVII, F374Y/L305V/M298Q/K337A/ V158T/S314E-FVII, F374Y/L305V/V158D/E296V/ M298Q/K337A-FVII, F374Y/L305V/V158D/E296V/ K337A/S314E-FVII, F374Y/L305V/V158D/M298Q/ K337A/S314E-FVII, F374Y/L305V/E296V/M298Q/ K337A/V158T/S314E-FVII, F374Y/L305V/V158D/ E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/ A292T-FVII, G291N-FVII, R315N/V317T-FVII, K143N/ N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

Thus, substitution variants in a factor VII polypeptide include, without limitation substitutions in positions P10, K32, L305, M306, D309, L305, L305, F374, V158, M298, V158, E296, K337, M298, M298, S336, S314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L305I, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

In some embodiments, the Factor VII polypeptide is human Factor VIIa (hFVIIa), preferably recombinantly made human Factor VIIa (rhVIIa).

In other embodiments, the Factor VII polypeptide is a Factor VII sequence variant.

In some embodiments, the Factor VII polypeptide has a glycosylation different from wild-type human Factor VII.

Cells

In practicing the present invention, the cells are eukaryote cells, more preferably an established eukaryote cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. A preferred CHO cell line is the CHO K1 cell line available from ATCC under accession number CCl61.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, *Proc. Natl. Acad. Sci. USA* 77:4216-4220, 1980) (DUKX cells also being referred to as DXB11 cells), and DG44 (CHO cell line) (*Cell*, 33: 405, 1983, and *Somatic Cell and Molecular Genetics* 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. Suitable insect cell lines also include, without limitation, *Lepidoptera* cell lines, such as *Spodoptera frugiperda* cells or *Trichoplusia ni* cells (see, e.g., U.S. Pat. No. 5,077,214).

In some embodiments, the cells used in practicing the invention are capable of growing in suspension cultures. As used herein, suspension-competent cells are those that can grow in suspension without making large, firm aggregates, i.e., cells that are monodisperse or grow in loose aggregates with only a few cells per aggregate. Suspension-competent cells include, without limitation, cells that grow in suspension without adaptation or manipulation (such as, e.g., hematopoietic cells or lymphoid cells) and cells that have been made suspension-competent by gradual adaptation of attachment-dependent cells (such as, e.g., epithelial or fibroblast cells) to suspension growth.

The cells used in practicing the invention may be adhesion cells (also known as anchorage-dependent or attachment-dependent cells). As used herein, adhesion cells are those that need to adhere or anchor themselves to a suitable surface for propagation and growth. In one embodiment of the invention, the cells used are adhesion cells. In these embodiments, both the propagation phases and the production phase include the use of microcarriers. The used adhesion cells should be able to migrate onto the carriers (and into the interior structure of the carriers if a macroporous carrier is used) during the propagation phase(s) and to migrate to new carriers when being transferred to the production bioreactor. If the adhesion cells are not sufficiently able to migrate to new carriers by themselves, they may be liberated from the carriers by contacting the cell-containing microcarriers with proteolytic enzymes or EDTA. The medium used (particularly when free of animal-derived components) should furthermore contain components suitable for supporting adhesion cells; suitable media for cultivation of adhesion cells are available from commercial suppliers, such as, e.g., Sigma.

The cells may also be suspension-adapted or suspension-competent cells. If such cells are used, the propagation of cells may be done in suspension, thus microcarriers are only used in the final propagation phase in the production culture vessel itself and in the production phase. In case of suspension-adapted cells the microcarriers used are typically macroporous carriers wherein the cells are attached by means of physical entrapment inside the internal structure of the carriers.

In such embodiments, the eukaryotic cell is typically selected from CHO, BHK, HEK293, myeloma cells, etc.

Cell Culture Procedures

The methods of the invention are typically performed in a stirred culture vessel and a microcarrier-based process type is preferably employed. In the microcarrier-based process the cells have migrated into the internal structure of the carriers (macroporous carriers) or have attached themselves to the surface of the carriers (solid carriers), or both. In a microcarrier-based process the eukaryote cells, the microcarriers and the cell culture liquid are supplied to a culture vessel initially. In the following days additional cell culture liquid may be fed if the culture volume was not brought to the final working volume of the vessel from the start. During the following period periodic harvest of product-containing culture supernatant and replacement with new medium liquid is performed, until the culture is finally terminated. When harvesting product-containing supernatant the agitation, e.g., stirring, of the culture is stopped and the cell-containing carriers are allowed to sediment following which part of the product-containing cell culture supernatant is removed.

In order to improve the overall outcome of the procedure, a cooling step may preferably be applied before harvesting of the product-containing supernatant, see, e.g., WO 03/029442. In some embodiments the culture liquid is cooled to a temperature between about 18° C. and about 32° C. before allowing the carriers to sediment, or between about 20° C. and about 30° C., or between about 22° C. and about 28° C.

Other applicable variants of the cell culture procedure are disclosed in WO 02/29084.

Propagation Steps

Before reaching the production phase where regular harvesting of product-containing culture supernatant for further down-stream processing is performed, the cells are propagated according to any scheme or routine that may be suitable for the particular cell in question. The propagation phase may be a single step or a multiple step procedure. In a single step propagation procedure the cells are removed from storage and inoculated directly to the culture vessel containing the microcarriers where the production is going to take place. In a multiple step propagation procedure the cells are removed from storage and propagated through a number of culture vessels of gradually increasing size until reaching the final culture vessel containing microcarriers where production is going to take place. During the propagation steps the cells are grown under conditions that are optimized for growth. Culture conditions, such as temperature, pH, dissolved oxygen tension, concentration of dissolved $CO_2$, and the like, are those known to be optimal for the particular cell and will be apparent to the skilled person or artisan within this field (see, e.g., *Animal Cell Culture: A Practical Approach* $2^{nd}$ Ed., Rickwood, D. and Hames, B. D., eds., Oxford University Press, New York (1992)).

In one approach, the cell culture process is operated in one culture vessel: The cells are inoculated directly into the culture vessel containing microcarriers where the production is going to take place; the cells are propagated until a suitable cell density is reached and the production phase is initiated.

In another approach, the cell culture process is operated in at least two distinct culture vessels: One or more seed culture vessel(s) (first propagation step(s)) followed by the production culture vessel (last propagation step followed by production phase). In the first propagation step the cells expressing the desired polypeptide are inoculated into a seed culture vessel containing culture medium and propagated until the cells reach a minimum cross-seeding density. Subsequently, the propagated seed culture is transferred to the production culture vessel containing (a) culture medium and (b) microcarriers. In this culture vessel the cells are cultured under conditions in which the cells migrate onto the surface of the solid carriers or the exterior and interior surfaces of the macroporous carriers, and they continue to grow in this last propagation step until the carriers are fully colonised by the cells. During this last propagation step medium exchange is performed by allowing the microcarriers to settle to the bottom of the culture vessel, after which a predetermined percentage of the tank volume of medium is removed and a corresponding percentage tank volume of fresh medium is added to the vessel. The microcarriers are then re-suspended in the medium and this process of medium removal and replacement are repeated at a predetermined interval, for example every 24 hours. The amount of replaced medium depends on the cell density and may typically be from 10-95%, preferably from 25% to 80%, of the tank volume as shown in Table 1 below.

It will be understood that in a process where the propagation phase is a multiple step procedure the propagation may take place in culture vessels of progressively increasing size until a sufficient number of cells is obtained for entering the final culture vessel. For example, one or more seed culture vessels of 5 L, 50 L, 100 L or 500 L may be used sequentially. A seed culture vessel typically has a capacity of between 5 L and 1000 L. Typically, cells are inoculated into a seed culture vessel at an initial density of about 0.2 to $0.4 \times 10^6$ cells/mL and propagated until the culture reaches a cell density of about $1.0 \times 10^6$ cells/mL. Typically, a minimum cross-seeding density is between about 0.8 and about $1.5 \times 10^6$ cells/mL.

Some of the set-points that are suitable for the production of a desired polypeptide, e.g., factor VII, are not necessarily suitable for the initial growth of the cells, either in seed culture or on the microcarriers. For example, temperature, dissolved oxygen tension, dissolved $CO_2$ concentration, and pH may be different for the two phases. The medium exchanges during propagation is done to keep the cells alive and growing, not to harvest culture supernatant for down-stream processing.

Possible culture conditions for the last propagation step in the final culture vessel (containing microcarriers) are outlined in Table 1, below.

TABLE 1

| Set-point | Range | Preferred range | Preferred Value A | Preferred Value B |
|---|---|---|---|---|
| Dissolved $CO_2$ concentration | 80-200 mmHg | 100-180 mmHg | 120-180 mmHg | 120-160 mm Hg |
| pH | 6-8 | 6.6-7.6 | 7.0 | 7.0 |
| Temperature | 28-40° C. | 34-38° C. | 35-37° C. | 36-37° C. |
| Dissolved Oxygen Tension | 10-90% of saturation | 20-80% of saturation | 50% of saturation | 50% of saturation |
| Daily Medium Change: | | | | |
| % of medium changed at | 10-35% of medium | 25% of medium exchanged at | 25% of medium exchanged at | 25% of medium exchanged at |

TABLE 1-continued

| Set-point | Range | Preferred range | Preferred Value A | Preferred Value B |
|---|---|---|---|---|
| | exchanged at 0.4-1.0 × 10⁶ cells/mL | 0.4-1.0 × 10⁶ cells/mL | 0.5 × 10⁶ cells/mL | 0.5 × 10⁶ cells/mL |
| % of medium changed at | 30-70% of medium exchanged at 0.7-3.0 × 10⁶ cells/mL | 50% of medium exchanged at 0.7-3.0 × 10⁶ cells/mL | 50% of medium exchanged at 1.0 × 10⁶ cells/mL | 50% of medium exchanged at 1.0 × 10⁶ cells/mL |
| % of medium changed at | 60-90% of medium exchanged at 1.0-12.0 × 10⁶ cells/mL | 80% of medium exchanged at 1.0-12.0 × 10⁶ cells/mL | 80% of medium exchanged at 2.0-10 × 10⁶ cells/mL | 80% of medium exchanged at 2.0-10 × 10⁶ cells/mL |

Production Phase

Besides the features and measures defined for the methods of the present invention, a number of other measures need to be taken for the production to yield a satisfactory outcome as will be described in the following.

When the cell density reaches the value suitable for start of production phase, i.e. for having product-containing culture supernatant down-stream processed, 60-95% of the culture supernatant is harvested every 24 hours, preferably 80%. This value of cell density is typically $1-12 \times 10^6$ cells/mL. Set-points may be changed at this point and set at values suitable for production of the desired polypeptide.

The medium exchange is performed by allowing the microcarriers to settle to the bottom of the tank, after which the selected percentage of the tank volume of medium is removed and a corresponding percentage tank volume of fresh medium is added to the vessel. Between 25 and 90% of the tank volume are typically replaced; preferably, 80% of the tank volume is replaced with fresh medium. The microcarriers are then re-suspended in the medium and this process of medium removal and replacement are typically repeated every 10 to 48 hours; preferably, every 24 hours.

An outline of this aspect of the process is shown in Table 2.

TABLE 2

| Set-point | Range | Preferred range | Preferred Value C | Preferred Value D |
|---|---|---|---|---|
| Dissolved CO₂ concentration | 80-200 mmHg | 100-180 mmHg | 120-180 mmHg | 120-160 mm Hg |
| pH | 6-8 | 6.6-7.6 | 7.0 for CHO and 6.7-6.9 for BHK | 7.0 for CHO and 6.7-6.9 for BHK |
| Temperature | 26-40° C. | 30-37° C. | 36° C. | 36° C. |
| Dissolved Oxygen Tension | 10-90% of saturation | 20-80% of saturation | 50% | 50% |
| % of medium changed | 25-90% of medium exchanged every 10-48 hours | 80% of medium changed every 10-48 hours | 80% of medium changed every 24 hours | 80% of medium changed every 24 hours |

Optionally, a drop in temperature set point of the cultivation may be employed when entering, and during, the production phase.

When entering the production phase temperature, dissolved oxygen tension, dissolved CO₂-concentration, operating pH and medium exchange frequency are typically changed to values that are optimal for production. Examples of temperature ranges and values in growth and production phase, respectively, can be seen from Tables 1 and 2. A temperature of about 36° C. is preferred for a CHO cell line during the production phase.

Microcarriers

As used herein, microcarriers are particles which are small enough to allow them to be used in suspension cultures (with a stirring rate that does not cause significant shear damage to cells). They are solid, porous, or have a solid core with a coating on the surface. Microcarriers may, for example, without limitation, be cellulose- or dextran-based, and their surfaces (exterior and interior surface in case of porous carriers) may be positively charged. Further details can be found in WO 02/29083 and in "Microcarrier cell culture, principles and methods. Amersham Pharmacia Biotech. 18-1140-62. Edition AA".

In one series of embodiments, the microcarriers have an overall particle diameter between about 150 and 350 um; and have a positive charge density of between about 0.8 and 2.0 meq/g. In one series of embodiments, the microcarrier is a solid carrier. Useful solid microcarriers include, without limitation, Cytodex 1™ and Cytodex 2™ (GE Healthcare). Solid carriers are particularly suitable for adhesion cells (anchorage-dependent cells).

In another series of embodiments, the microcarrier is a macroporous carrier. As used herein, macroporous carriers are particles, e.g. cellulose-based, which have the following properties: (a) They are small enough to allow them to be used in suspension cultures (with a stirring rate that does not cause significant shear damage to cells); and (b) they have pores and interior spaces of sufficient size to allow cells to migrate into the interior spaces of the particle. Their surfaces (exterior and interior) may in one embodiment be positively charged. In one series of embodiments, the carriers: (a) have an overall particle diameter between about 150 and 350 um; (b) have pores having an average pore opening diameter of between about 15 and about 40 um; and (c) have a positive charge density of between about 0.8 and 2.0 meq/g. In some embodiments, the positive charge is provided by DEAE (N,N,-diethylaminoethyl) groups. Useful macroporous carriers include, without limitation, Cytopore 1™ and Cytopore 2™ (GE Healthcare). Particularly preferred are Cytopore 1™ carriers, which have a mean particle diameter of 230 um, an average pore size of 30 um, and a positive charge density of 1.1 meq/g.

Large-Scale Culture Conditions

As used herein, a large-scale culture vessel has a capacity of at least about 100 L, preferably at least about 500 L, more preferably at least about 1000 L and most preferably at least about 5000 L. In case that the cell culture process is operated in at least two distinct culture vessels, such as one or more seed culture vessel(s) (first propagation step(s)) followed by the production culture vessel (last propagation step followed by production phase), then the process typically involves transferring about 50 L of the propagated seed culture (having about $1.0 \times 10^6$ cells/mL) into a 500 L culture vessel containing 150 L of culture medium. The large-scale culture is maintained under appropriate conditions of, e.g., temperature, pH, dissolved oxygen tension (DOT), dissolved $CO_2$ concentration, and agitation rate, and the volume is gradually increased by adding medium to the culture vessel. In case of a microcarrier process the culture vessel also comprises an amount of microcarriers corresponding to a final microcarrier concentration in the range of 1 to 10 g/L. After the transfer, the cells typically migrate onto the surface of the carriers or into the interior of the carriers within the first 24 hours.

Medium

The terms "cell culture liquid" and "culture medium" (or simply "medium") refer to a nutrient solution used for growing eukaryote cells that typically provides at least one component from one or more of the following categories: (1) salts of e.g. sodium, potassium, magnesium, and calcium contributing to the osmolality of the medium; (2) an energy source, usually in the form of a carbohydrate such as glucose; (3) all essential amino acids, and usually the basic set of twenty amino acids; (4) vitamins and/or other organic compounds required at low concentrations; and (5) trace elements, where trace elements are defined as inorganic compounds that are typically required at very low concentrations, usually in the micromolar range. The nutrient solution may optionally be supplemented with one or more of the components from any of the following categories: (a) hormones and other growth factors such as, for example, insulin, transferrin, and epidermal growth factor; and (b) hydrolysates of protein and tissues. Preferably, the cell culture medium does not contain any components of animal origin.

Importantly, the cell culture liquid comprises a plant protein hydrolysate as defined further above.

The present invention encompasses cultivating eukaryote cells in medium lacking animal-derived components. As used herein, "animal-derived" components are any components that are produced in an intact animal (such as, e.g., proteins isolated and purified from serum), or produced by using components produced in an intact animal (such as, e.g., an amino acid made by using an enzyme isolated and purified from an animal to hydrolyse a plant source material). By contrast, a protein which has the sequence of an animal protein (i.e., has a genomic origin in an animal) but which is produced in vitro in cell culture (such as, e.g., in a recombinant yeast or bacterial cell or in an established continuous eukaryote cell line, recombinant or not), in media lacking components that are produced in, and isolated and purified from an intact animal is not an "animal-derived" component (such as, e.g., insulin produced in a yeast or a bacterial cell, or insulin produced in an established mammalian cell line, such as, e.g., CHO, BHK or HEK cells, or interferon produced in Namalwa cells). For example, a protein which has the sequence of an animal protein (i.e., has a genomic origin in an animal) but which is produced in a recombinant cell in media lacking animal derived components (such as, e.g., insulin produced in a yeast or bacterial cell) is not an "animal-derived component". Accordingly, a cell culture medium lacking animal-derived components is one that may contain animal proteins that are recombinantly produced; such medium, however, does not contain, e.g., animal serum or proteins or other products purified from animal serum. Such medium may, for example, contain one or more components derived from plants. Any cell culture medium, in particular one lacking animal-derived components, that supports cell growth and maintenance under the conditions of the invention may be used. Typically, the medium contains water, an osmolality regulator, a buffer, an energy source, amino acids, an inorganic or recombinant iron source, one or more synthetic or recombinant growth factors, vitamins, and cofactors. In one embodiment, the medium lacks animal-derived components and lacks proteins ("protein-free"). Media lacking animal-derived components and/or proteins are available from commercial suppliers, such as, for example, Sigma, SAFC Biosciences, Gibco and Gemini.

In addition to conventional components, a medium suitable for producing Factor VII or Factor VII-related polypeptides contains Vitamin K, which is required for γ-carboxylation of glutamic acid residues in factor VII, at a concentration between about 0.1-50 mg/L, preferably between about 0.5-25 mg/L, more preferably between about 1-10 mg/L and most preferably about 5 mg/L.

Suitable media for use in the present invention are available from commercial suppliers such as, for example, Gibco, and SAFC Biosciences.

In one embodiment, the medium is composed as shown in Table 3a

The table below (Table 3a) is a composition of a medium suitable for use in the present invention.

TABLE 3a

| COMPONENT | Range (mg/L) |
| --- | --- |
| Sodium chloride | 0-70,000 |
| Potassium chloride | 0-3118 |
| Sodium dihydrogen phosphate monohydrate | 0-625 |
| Sodium hydrogen carbonate | 0-27 |
| Disodium hydrogen phosphate anhydrous | 0-710 |
| Disodium hydrogen phosphate heptahydrate | 0-1340 |
| Magnesium chloride anhydrous | 0-287 |
| Magnesium chloride hexahydrate | 0-610 |
| Magnesium sulphate anhydrous | 0-488 |
| Magnesium sulphate heptahydrate | 0-1000 |
| Calcium chloride anhydrous | 0-1166 |
| Copper sulphate pentahydrate | 0-0.014 |
| Ferrous sulphate heptahydrate | 0-4.17 |
| Ferric nitrate nonahydrate | 0-0.5 |
| Ferric citrate | 0-123 |
| Zinc sulphate heptahydrate | 0-0.44 |
| Dextrose anhydrous | 0-45,000 |
| Linoleic acid | 0-12 |
| Insulin | 0-50 |
| DL 68 Thioctic Acid | 0-9 |
| L-alanine | 0-50 |
| L-arginine chloride | 0-5500 |
| L-asparagine monohydrate | 0-6010 |

TABLE 3a-continued

| COMPONENT | Range (mg/L) |
|---|---|
| L-aspartic acid | 0-1100 |
| L-cysteine hydrochloride monohydrate | 0-1200 |
| L-glutamic acid | 0-2500 |
| Glycine | 0-190 |
| L-histidine hydrochloride monohydrate | 0-2200 |
| L-isoleucine | 0-750 |
| L-leucine | 0-1800 |
| L-lysine hydrochloride | 0-2400 |
| L-methionine | 0-1380 |
| L-phenylalanine | 0-1600 |
| L-proline | 0-1150 |
| L-serine | 0-4300 |
| L-threonine | 0-1800 |
| L-tryptophan | 0-2100 |
| L-tyrosine disodium dihydrate | 0-900 |
| L-valine | 0-1800 |
| L-cystine dihydrochloride | 0-320 |
| Sodium hypoxanthine | 0-25 |
| Putrescine dihydrochloride | 0-1 |
| Sodium pyruvate | 0-2300 |
| D-Biotin | 0-3 |
| D-calcium pantothenate | 0-60 |
| Folic acid | 0-70 |
| I-inositol | 0-700 |
| Nicotinamide | 0-50 |
| Choline chloride | 0-450 |
| Pyridoxine hydrochloride | 0-25 |
| Riboflavin | 0-3 |
| Thiamine hydrochloride | 0-35 |
| Thymidine | 0-4 |
| Vitamin B12 | 0-50 |
| Pyridoxal hydrochloride | 0-60 |
| Glutathione | 0-50 |
| Sodium Selenite | 0-0.5 |
| L-ascorbic acid | 0-50 |
| Pluronic F68 | 0-10,000 |
| Vitamin K | 0-50 |
| Dextran T 70 | 0-1000 |
| Plant protein hydrolysate | 200-10000 |
| Lipids | 0-15 |
| Oleic acid | |
| Growth Factors HGR, IGF, EGF | 0-50 |

In one embodiment, the medium is composed as shown in Table 3b

The table below (Table 3b) is a composition of a medium suitable for use in the present invention.

TABLE 3b

| COMPONENT | Range (mg/L) |
|---|---|
| Sodium chloride | 0-70,000 |
| Potassium chloride | 0-3118 |
| Sodium dihydrogen phosphate monohydrate | 0-625 |
| Sodium hydrogen carbonate | 0-5000 |
| Disodium hydrogen phosphate anhydrous | 0-710 |
| Disodium hydrogen phosphate heptahydrate | 0-1340 |
| Magnesium chloride anhydrous | 0-287 |
| Magnesium chloride hexahydrate | 0-610 |
| Magnesium sulphate anhydrous | 0-488 |
| Magnesium sulphate heptahydrate | 0-1000 |

TABLE 3b-continued

| COMPONENT | Range (mg/L) |
|---|---|
| Calcium chloride anhydrous | 0-1166 |
| Copper sulphate pentahydrate | 0-0.014 |
| Ferrous sulphate heptahydrate | 0-4.17 |
| Ferric nitrate nonahydrate | 0-0.5 |
| Ferric citrate | 0-123 |
| Zinc sulphate heptahydrate | 0-0.44 |
| Dextrose anhydrous | 0-45,000 |
| Linoleic acid | 0-12 |
| Insulin | 0-50 |
| DL 68 Thioctic Acid | 0-9 |
| L-alanine | 0-50 |
| L-arginine chloride | 0-5500 |
| L-asparagine monohydrate | 0-6010 |
| L-aspartic acid | 0-1100 |
| L-cysteine hydrochloride monohydrate | 0-1200 |
| L-glutamic acid | 0-2500 |
| Glycine | 0-190 |
| L-histidine hydrochloride monohydrate | 0-2200 |
| L-isoleucine | 0-750 |
| L-leucine | 0-1800 |
| L-lysine hydrochloride | 0-2400 |
| L-methionine | 0-1380 |
| L-phenylalanine | 0-1600 |
| L-proline | 0-1150 |
| L-serine | 0-4300 |
| L-threonine | 0-1800 |
| L-tryptophan | 0-2100 |
| L-tyrosine disodium dihydrate | 0-900 |
| L-valine | 0-1800 |
| L-cystine dihydrochloride | 0-320 |
| Sodium hypoxanthine | 0-25 |
| Putrescine dihydrochloride | 0-1 |
| Sodium pyruvate | 0-2300 |
| D-Biotin | 0-3 |
| D-calcium pantothenate | 0-60 |
| Folic acid | 0-70 |
| I-inositol | 0-700 |
| Nicotinamide | 0-50 |
| Choline chloride | 0-450 |
| Pyridoxine hydrochloride | 0-25 |
| Riboflavin | 0-3 |
| Thiamine hydrochloride | 0-35 |
| Thymidine | 0-4 |
| Vitamin B12 | 0-50 |
| Pyridoxal hydrochloride | 0-60 |
| Glutathione | 0-50 |
| Sodium Selenite | 0-0.5 |
| L-ascorbic acid | 0-50 |
| Pluronic F68 | 0-10,000 |
| Vitamin K | 0-50 |
| Dextran T 70 | 0-1000 |
| Plant protein hydrolysate | 200-10000 |
| Lipids | 0-15 |
| Oleic acid | |
| Growth Factors HGR, IGF, EGF | 0-50 |

The medium is preferably a medium lacking animal-derived components.

In one embodiment the medium is a commercially available protein-free CHO medium lacking animal-derived components (SAFC Biosciences).

In some embodiments, the cells used in practicing the present invention are adapted to suspension growth in medium lacking animal-derived components, such as, e.g., medium lacking serum. Such adaptation procedures are described, e.g., in Scharfenberg, et al., *Animal Cell Technology Developments towards the 21$^{st}$ Century*, E. C. Beuvery et al. (Eds.), Kluwer Academic Publishers, pp. 619-623, 1995

(BHK and CHO cells); Cruz, *Biotechnol. Tech.* 11:117-120, 1997 (insect cells); Keen, *Cytotechnol.* 17:203-211, 1995 (myeloma cells); Berg et al., *Biotechniques* 14:972-978, 1993 (human kidney 293 cells). In a particularly preferred embodiment, the host cells are BHK 21 or CHO or HEK 293 cells that have been engineered to express human Factor VII and that have been adapted to grow in the absence of serum or animal-derived components.

Culture Vessel

Culture vessels applicable within the present invention may, e.g., be based on conventional stirred tank reactors (CSTR) where agitation is obtained by means of conventional impeller types or airlift reactors where agitation is obtained by means of introducing air from the bottom of the vessel. Among the further parameters that are typically controlled within specified limits are pH, dissolved oxygen tension (DOT), concentration of dissolved $CO_2$ and temperature. Dissolved oxygen tension may be maintained by, e.g., sparging with pure oxygen. The concentration of dissolved $CO_2$ may be maintained by sparging with air. The temperature-control medium is typically water, heated or cooled as necessary. The water may be passed through a jacket surrounding the vessel or through a piping coil immersed in the culture.

The term "culture vessel" may be used interchangeably with "tank", "reactor", "fermentor" and "bioreactor".

Downstream Processing

Once the medium has been removed from the culture vessel, it may be subjected to one or more processing steps to obtain the desired protein, including, without limitation, centrifugation or filtration to remove cells that were not immobilized in the carriers; affinity chromatography, hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J.-C. Janson and Lars Ryden, editors, VCH Publishers, New York, 1989.

Purification of Factor VII or Factor VII-related polypeptides may involve, e.g., affinity chromatography on an anti-Factor VII antibody column (see, e.g., Wakabayashi et al., *J. Biol. Chem.* 261:11097, 1986; and Thim et al., *Biochem.* 27:7785, 1988) and activation by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, Factor VII may be activated by passing it through an ion-exchange chromatography column, such as Mono Q® (Pharmacia) or the like.

The following examples are intended as non-limiting illustrations of the present invention.

EXAMPLES

Example 1

Serum-Free Production of Factor VII (Small Pilot-Scale Culture)

The following experiment was performed to produce Factor VII in a small pilot-scale culture (20 L). A flow sheet of the cultivation process is shown in FIG. 1. The production part of the process is a high-cell-density (HCD) process in which the cells are retained in the fermentor by means of microcarriers.

Cells were thawed from a cell bank of the FVII producer cell line. The FVII producer cell line was a CHO K1 cell line transfected with Factor VII-encoding gene and adapted to grow in serum-free suspension in the absence of animal-derived components. After thawing, the cells were propagated sequentially in spinner bottles of increasing size in a liquid medium free of animal derived components. The medium used for propagation had a concentration of soy protein hydrolysate of around 5.0 g/L. As the cell number increased, the volume was gradually increased by addition of new medium. The medium used was free of serum and other animal derived components. When the volume had reached 4 L, and the cell number had reached $\approx 0.8*10^6$/ml, the contents of the spinner bottles were transferred into a 20 L stirred tank reactor (small pilot-scale production fermentor). The production fermentor contained macroporous Cytopore carriers (GE Healthcare), and after transfer of cells to the production fermentor, the cells were immobilised in the carriers within 24 hours. The volume in the production fermentor was gradually increased by addition of new medium as the cell number increased. After some days, when the volume has reached 20 L the production phase was initiated. The medium used in the production fermentor had a concentration of soy protein hydrolysate of 1.25 g/L (Embodiment a) or 5.0 g/L (Reference).

During the production phase a medium exchange was performed every 24 hours: Agitation was stopped to allow for sedimentation of the carriers, and about 80% of the culture supernatant was then harvested and replaced with new medium. The harvested culture supernatant was transferred for down stream processing. The process was run in production phase in this way for several weeks. The culture in the production fermentor was maintained at a temperature of around 36° C., at a dissolved oxygen level of around 50% of saturation with air, and at a dissolved $CO_2$ level of around 100-150 mmHg. During the production phase the cell density reached $1\text{-}2 \times 10^7$ cells/ml, and the FVII concentration in the daily harvest 10-20 mg/L. The pH was kept above 6.70.

Figure 2:
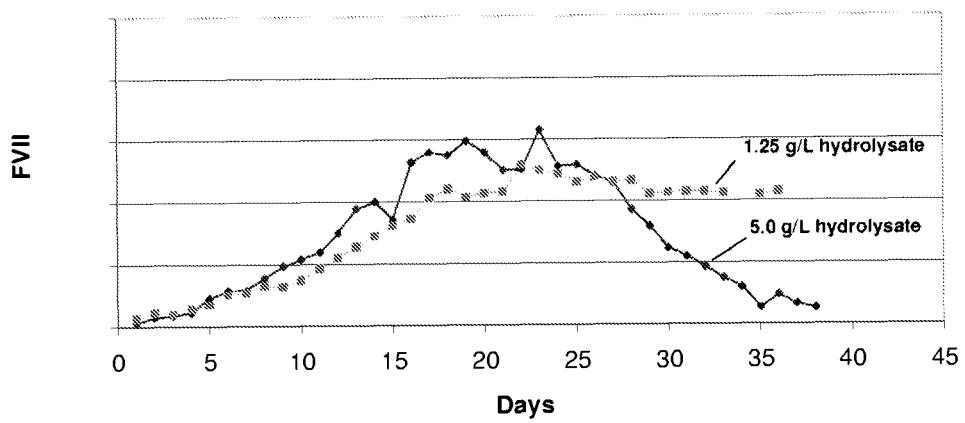
FIG. 2 shows a graph with the results from microcarrier cultivation in a 20 L fermentor, cf. Example 1.

The graphs in FIG. 2 show results from microcarrier cultivations in 20 L fermentors (small pilot scale fermentors). The graphs illustrate a difference in stability with regard to Factor VII productivity when using 1.25 g/L soy hydrolysate instead of 5.0 g/l soy hydrolysate in the production fermentor.

Example 2

Serum-Free Production of Factor VII (Large Pilot-Scale Culture)

Cells were thawed from a cell bank of the FVII producer cell line. The FVII producer cell line was a CHO K1 cell line transfected with Factor VII-encoding gene and adapted to grow in serum-free suspension in the absence of animal-derived components. After thawing, the cells were propagated sequentially in spinner bottles of increasing size in a liquid medium free of animal derived components. The medium used for propagation had a concentration of soy protein hydrolysate of around 5.0 g/L. As the cell number increased, the volume was gradually increased by addition of new medium. The medium used was free of serum and other animal derived components. When the volume had reached 4 L, and the cell number had reached $\approx 0.8*10^6$/ml, the contents of the spinner bottles were transferred into a 50 L stirred tank reactor (seed fermentor). The medium used for propagation in the 50 L fermentor had a concentration of soy protein hydrolysate of around 5.0 g/L. As the cell number increased, the volume was gradually increased by addition of new medium. The medium used was free of serum and other animal derived components. When the volume had reached 50 L, and the cell number had reached ≈$1.0*10^6$/ml, the contents of the 50 L fermentor were transferred into a 500 L stirred tank reactor (large pilot-scale production fermentor). The production fermentor contained macroporous Cytopore carriers (GE Healthcare), and after transfer of cells to the production fermentor, the cells were immobilised in the carriers within 24 hours. The volume in the production fermentor was gradually increased by addition of new medium as the cell number increased. After some days, when the volume has reached 450 L the production phase was initiated. The medium used in the propagation phase of the production fermentor had a concentration of soy protein hydrolysate of 5 g/L while the medium used in the production phase had a concentration of soy protein hydrolysate of 1 g/L (Embodiment a). In a Reference run the medium had a concentration of soy protein hydrolysate in propagation as well as production phase.

During the production phase a medium exchange was performed every 24 hours: Agitation was stopped to allow for sedimentation of the carriers, and about 80% of the culture supernatant was then harvested and replaced with new medium. The harvested culture supernatant was transferred for down stream processing. The process was run in production phase in this way for several weeks. The culture in the production fermentor was maintained at a temperature of around 36° C., at a dissolved oxygen level of around 50% of saturation with air, and at a dissolved $CO_2$ level of around 100-150 mmHg. During the production phase the cell density reached $1-2\times10^7$ cells/ml, and the FVII concentration in the daily harvest 10-20 mg/L. The pH was kept above 6.70.

Figure 3:
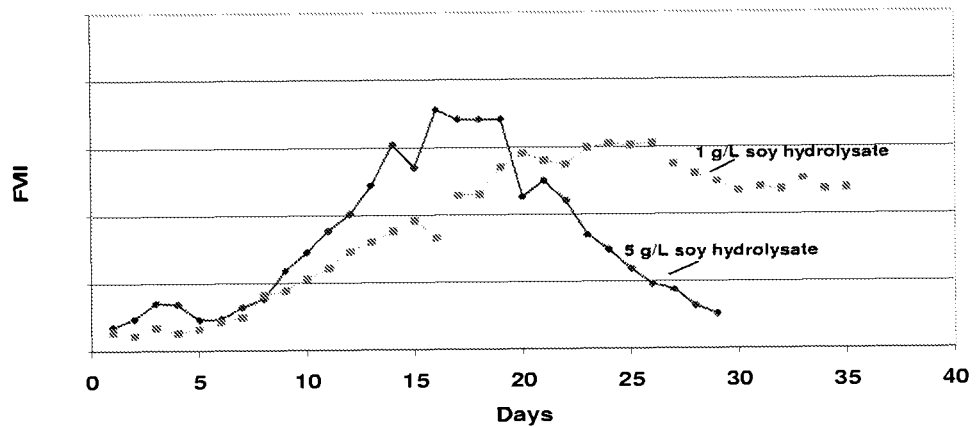
FIG. 3 shows a graph with the results from microcarrier cultivation in a 500 L fermentor, cf. Example 2.

The graphs in FIG. 3 show results from microcarrier cultivations in 500 L fermentors (large pilot scale fermentors). The graphs illustrate a difference in stability with regard to Factor VII productivity when using 1 g/L soy hydrolysate instead of 5 g/l soy hydrolysate in the production phase of the production fermentor.

Example 3

Serum-Free Production of Factor VII (Large Scale)

Cells are thawed from a cell bank of the FVII producer cell line. The FVII producer cell line is a CHO cell line transfected with Factor VII-encoding gene and adapted to growth in serum free suspension. After thawing the cells are propagated sequentially in spinner bottles of increasing size. As the cell number increases, the volume is gradually increased by addition of new medium. The medium used is free of serum and other animal derived components. Finally, 4 L of spinner culture are transferred to the first seed fermentor step (50 L fermentor). As the cell number increases, the volume in the seed fermentor is gradually increased to 50 L. The 50 L of seed culture are then transferred to the second seed fermentor step (500 L fermentor). As the cell number increases in the 500 L seed fermentor, the volume is gradually increased to 500 L. The production fermentor (5000 L) contains macroporous Cytopore carriers (GE Healthcare), and after transfer of cells to the production fermentor, the cells are immobilised in the carriers within 24 hours. The volume in the production fermentor is gradually increased by addition of new medium as the cell number increases. The medium in spinner bottles, seed fermentors and the propagation phase of the production fermentor has a concentration ($C_1$) of soy bean hydrolysate of about 5 g/L. After some days, when the volume has reached 4500 L, the production phase is initiated. During the production phase a medium exchange is performed every 24 hours: Agitation is stopped to allow for sedimentation of the carriers, and about 80% of the culture supernatant is then harvested and replaced with new medium. The medium in the production phase has a concentration ($C_2$) of soy bean hydrolysate of about 1 g/L. The harvested culture supernatant is transferred for down stream processing. The process is run in production phase in this way for several weeks. The culture in the production fermentor is maintained at a temperature of around 36° C., at a dissolved oxygen level of around 50% of saturation with air, and at a dissolved $CO_2$ level in the range 100-180 mmHg, such as, e.g., 100-150 mm Hg. All bioreactors (50 L, 500 L, 5000 L) are instrumented for control of temperature, dissolved oxygen (sparging of oxygen through microsparger), agitation rate, headspace aeration rate and pH (downwards control by addition of $CO_2$ gas to headspace, no upwards control by addition of base). Furthermore, the production fermentor (5000 L) is instrumented for control of dissolved $CO_2$. Online $CO_2$ measurement is performed by means of an YSI 8500 $CO_2$-instrument. The level of $CO_2$ is controlled by sparging of atmospheric air into the liquid through a tube according to the $CO_2$ signal. The sparging rate is set to 0 L/min per L of culture liquid when the $CO_2$ concentration is at or below the set-point, and to 0.01-0.05 L/min per L of culture liquid when the $CO_2$ concentration is above the set-point. During the production phase the cell density reaches $1-2\times10^7$ cells/ml, and the FVII concentration in the daily harvest 10-20 mg/L. The pH is kept above 6.70.

The invention claimed is:

1. A method for large-scale production of a polypeptide in eukaryote cells contained in a serum-free culture liquid, said method comprising
    (i) a propagation phase for said cells, where the cells are propagated in a first cell culture liquid, and
    (ii) a production phase for said cells, where the cells are present in a second cell culture liquid,
wherein each of the cell culture liquids comprise a plant protein hydrolysate, and wherein the ratio between the concentration of the plant protein hydrolysate ($C_1$) in the first cell culture liquid and the concentration of the plant protein hydrolysate ($C_2$) in the second cell culture liquid is at least 1.5:1 ($C_1$:$C_2$).

2. The method according to claim 1, wherein the ratio $C_1$:$C_2$ is in the range of 2:1 to 10:1.

3. The method according to claim 2, wherein the concentration $C_2$ is in the range of 0.2-3.5 g/L.

4. The method according to claim 3, wherein the concentration $C_1$ is in the range of 4.0-10.0 g/L.

5. The method according to claim 4, wherein the plant protein hydrolysate is soy protein hydrolysate.

6. The method according to claim 5, wherein the polypeptide is a Factor VII polypeptide.

7. A method for large-scale production of a Factor VII polypeptide in eukaryote cells contained in a serum-free culture liquid, said method comprising
    (i) a propagation phase for said cells, where the cells are propagated in a first cell culture liquid, and
    (ii) a production phase for said cells, where the cells are present in a second cell culture liquid,
wherein the first cell culture liquid comprises a soy protein hydrolysate in a concentration of 4.0-10.0 g/L, the second cell culture liquid comprises a soy protein hydrolysate in a concentration of 0.2-3.5 g/L, and wherein the ratio between the concentration of the soy protein hydrolysate ($C_1$) in the first cell culture liquid and the concentration of the soy protein hydrolysate ($C_2$) in the second cell culture liquid is at least 1.5:1 ($C_1$:$C_2$).

8. A method for large-scale production of a Factor VII polypeptide in eukaryote cells contained in a serum-free culture liquid, said method comprising
   (i) a propagation phase for said cells, where the cells are propagated in a first cell culture liquid, and
   (ii) a production phase for said cells, where the cells are present in a second cell culture liquid,
wherein each of the cell culture liquids comprise a plant protein hydrolysate, and wherein the concentration of the plant protein hydrolysate ($C_2$) in the second cell culture liquid is in the range of 0.7-3.0 g/L.

9. The method according to claim 8, wherein the concentration $C_2$ is in the range of 0.9-2.5 g/L.

10. The method according to claim 9, wherein each of the cell culture liquids comprise a plant protein hydrolysate, and wherein the ratio between the concentration of the plant protein hydrolysate ($C_1$) in the first cell culture liquid and the concentration of the plant protein hydrolysate ($C_2$) in the second cell culture liquid is at least 1.5:1.

11. The method according to claim 10, wherein the concentration $C_1$ is in the range of 4.0-10.0 g/L.

12. The method according to claim 1, wherein the concentration of the plant protein hydrolysate observed against time of fermentation has the following profile:
   high concentration in the propagation phase ($C_1$);
   low concentration in the production phase—low level A ($C_{2A}$);
   low concentration in the production phase—low level B ($C_{2B}$);
   low concentration in the production phase—low level A ($C_{2A}$);
   low concentration in the production phase—low level B ($C_{2B}$);
   where $C_1 \gg C_{2B} > C_{2A}$ and the concentrations $C_{2A}$ and $C_{2B}$ are within the concentration ranges specified for $C_2$, and wherein a first switch from low level A ($C_{2A}$) to low level B ($C_{2B}$) is conducted when a decrease in the cell number is observed and a subsequent switch from low level B ($C_{2B}$) to low level A ($C_{2A}$) is conducted when the cell number has been restored to a level approximately corresponding to the level before the decrease.

13. The method according to claim 6, wherein the concentration of the plant protein hydrolysate observed against time of fermentation has the following profile:
   high concentration in the propagation phase ($C_1$);
   low concentration in the production phase—low level A ($C_{2A}$);
   low concentration in the production phase—low level B ($C_{2B}$);
   low concentration in the production phase—low level A ($C_{2A}$);
   low concentration in the production phase—low level B ($C_{2B}$);
   where $C_1 \gg C_{2B} > C_{2A}$ and the concentrations $C_{2A}$ and $C_{2B}$ are within the concentration ranges specified for $C_2$, and wherein a first switch from low level A ($C_{2A}$) to low level B ($C_{2B}$) is conducted when a decrease in the cell number is observed and a subsequent switch from low level B ($C_{2B}$) to low level A ($C_{2A}$) is conducted when the cell number has been restored to a level approximately corresponding to the level before the decrease.

14. The method according to claim 7, wherein the concentration of the plant protein hydrolysate observed against time of fermentation has the following profile:
   high concentration in the propagation phase ($C_1$);
   low concentration in the production phase—low level A ($C_{2A}$);
   low concentration in the production phase—low level B ($C_{2B}$);
   low concentration in the production phase—low level A ($C_{2A}$);
   low concentration in the production phase—low level B ($C_{2B}$);
   where $C_1 \gg C_{2B} > C_{2A}$ and the concentrations $C_{2A}$ and $C_{2B}$ are within the concentration ranges specified for $C_2$, and wherein a first switch from low level A ($C_{2A}$) to low level B ($C_{2B}$) is conducted when a decrease in the cell number is observed and a subsequent switch from low level B ($C_{2B}$) to low level A ($C_{2A}$) is conducted when the cell number has been restored to a level approximately corresponding to the level before the decrease.

15. The method according to claim 8, wherein the concentration of the plant protein hydrolysate observed against time of fermentation has the following profile:
   high concentration in the propagation phase ($C_1$);
   low concentration in the production phase—low level A ($C_{2A}$);
   low concentration in the production phase—low level B ($C_{2B}$);
   low concentration in the production phase—low level A ($C_{2A}$);
   low concentration in the production phase—low level B ($C_{2B}$);
   where $C_1 \gg C_{2B} > C_{2A}$ and the concentrations $C_{2A}$ and $C_{2B}$ are within the concentration ranges specified for $C_2$, and wherein a first switch from low level A ($C_{2A}$) to low level B ($C_{2B}$) is conducted when a decrease in the cell number is observed and a subsequent switch from low level B ($C_{2B}$) to low level A ($C_{2A}$) is conducted when the cell number has been restored to a level approximately corresponding to the level before the decrease.

16. The method according to claim 1, wherein the concentration $C_2$ is in the range of 0.2-3.5 g/L.

17. The method according to claim 1, wherein the concentration $C_1$ is in the range of 4.0-10.0 g/L.

18. The method according to claim 1, wherein the plant protein hydrolysate is soy protein hydrolysate.

19. The method according to claim 1, wherein the polypeptide is a Factor VII polypeptide.

20. The method according to claim 8, wherein each of the cell culture liquids comprise a plant protein hydrolysate, and wherein the ratio between the concentration of the plant protein hydrolysate ($C_1$) in the first cell culture liquid and the concentration of the plant protein hydrolysate ($C_2$) in the second cell culture liquid is at least 1.5:1.

* * * * *

UNITED STATES PATENT AND TRADEMARK OFFICE
CERTIFICATE OF CORRECTION

| | | |
|---|---|---|
| PATENT NO. | : 8,530,192 B2 | Page 1 of 1 |
| APPLICATION NO. | : 11/815880 | |
| DATED | : September 10, 2013 | |
| INVENTOR(S) | : Knudsen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1251 days.

Signed and Sealed this
Third Day of March, 2015

Michelle K. Lee
*Deputy Director of the United States Patent and Trademark Office*